METHOD FOR OBTAINING PROTECTIVE ACTIVE AND INACTIVE ADENYLATE CYCLASE FROM *BORDETELLA PARAPERTUSSIS*

US005595901A
United States Patent [19]
Rocancourt et al.
[11] Patent Number: 5,595,901
[45] Date of Patent: Jan. 21, 1997
[54] **METHOD FOR OBTAINING PROTECTIVE ACTIVE AND INACTIVE ADENYLATE CYCLASE FROM *BORDETELLA PARAPERTUSSIS***
[75] Inventors: Murielle Rocancourt, Clamart; **Colette Brezin

This application is a continuation of application Ser. No. 07/844,487 filed Mar. 4, 1992, abandoned, which is a continuation of application Ser. No. 07/340,551, filed Apr. 19, 1989, abandoned.

BACKGROUND OF THE INVENTION

The invention relates to a method for obtaining protective antigens against Bordetella infections and toxic processes.

It is well known that *B.pertussis* and *B.parapertussis* are both causative agents of whooping cough outbreaks.

Studies on the virulence factors prominently involved in the pathogenesis of whooping cough have led to consider two major products of *B.pertussis*, the filamentous hemagglutinin (FHA) and the pertussis toxin (Ptx), as major determinants of pathogenesis and as efficient immunogens.

In a previous work (FR patent application 8615968 of Nov. 17, 1986 in the names of Institut Pasteur and Inserm), the inventors have used antibodies raised against one other product synthesized by *B.pertussis*, the adenylate cyclase (AC), to demonstrate the role of this molecule as major toxin in the pulmonary cytopathic syndrome, as evidenced by the induction of an acute adematous hemorragic alveolitis (AEHA) in mice, and thus, as potential protective antigen.

SUMMARY OF THE INVENTION

It is then an object of the invention, using a Bordetella species different from *B.pertussis*, to provide adenylate cyclase preparations useful as protective antigens against whooping cough.

DETAILED DESCRIPTION OF THE PREFERRED EMBODIMENTS

Figure 1:
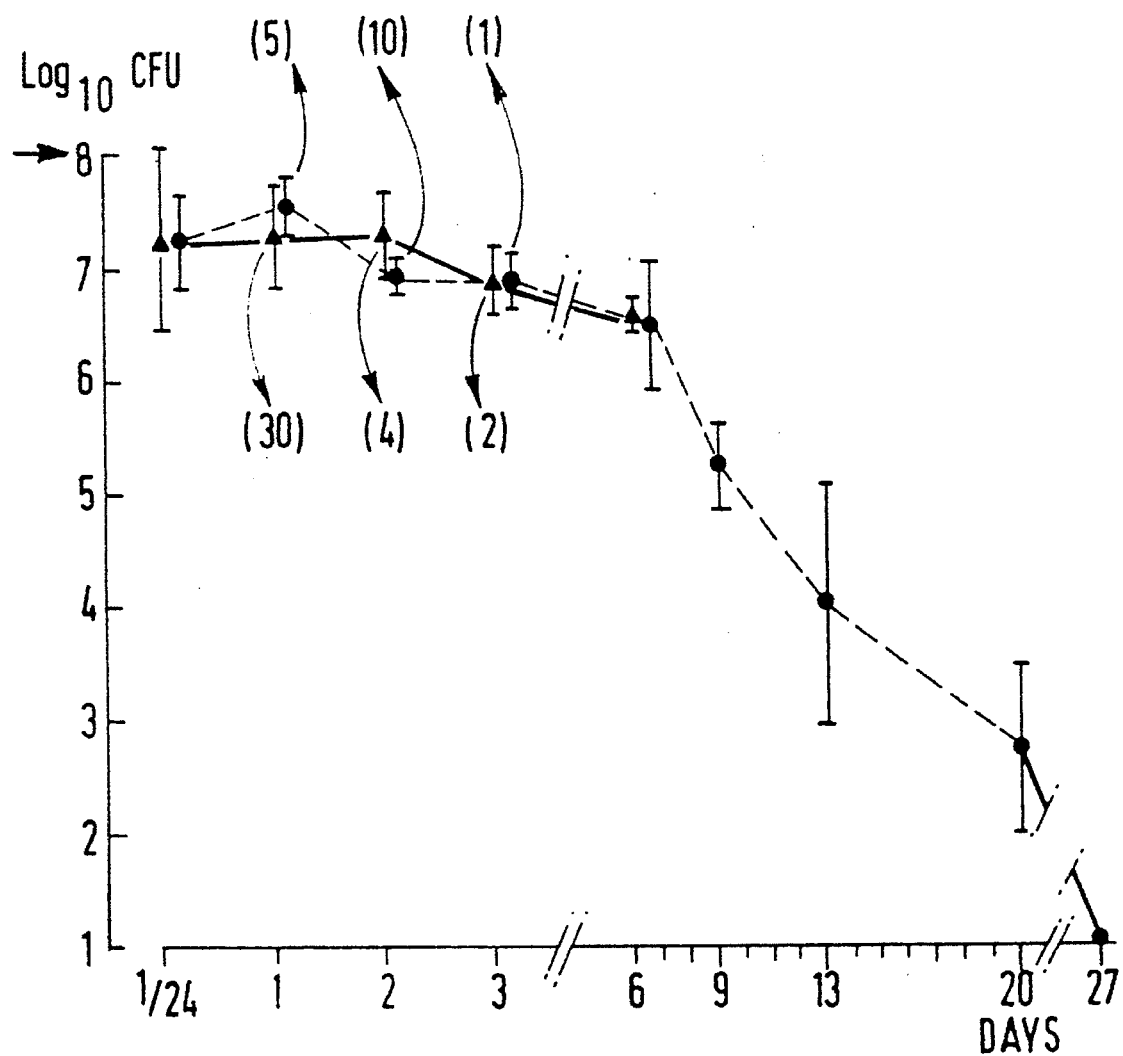
FIG. 1 represents the kinetics of pulmonary infection with *B. parapertussis* clones.

The inventors have now investigated the role of an adenylate cyclase produced and released by another Bordetella species and have investigated its role in the pathogenesis and immunity in an experimental infection of the mouse.

The method of the invention for obtaining an active adenylate cyclase and/or a cross-reactive, otherwise inactive protein, is characterized by the use of *B.parapertussis* or variants thereof.

It has to be noted that the terms "active" or "inactive" as used in the specification refer to the adenylate cyclase enzymatic activity.

The active adenylate cyclase has a molecular weight of about 43±4.3–45±4.5 kDa (molecular weight range Mr as determined with respect to ovalbumin used as standard). It is specifically recognized by specific polyclonal and monoclonal anti-*B.pertussis* AC antibodies.

Said active adenylate cyclase is capable of antigenically cross-reacting with the *B.pertussis* AC.

Said adenylate cyclase which is a cytotoxin responsible for the local pulmonary lesions occuring in whooping cough is advantageously endowed with immunogenic properties.

The inactive protein is disclosed in EP patent application filed on the same day, in the name of applicants, relating to "Immunoprotective antigenic protein against pathogenic bacteria".

Said inactive protein has a molecular weight of 43±4.33 KDa. It is specifically recognized by polyclonal anti-AC antibodies raised against purified AC preparations, and is devoid of adenylate cyclase, calmodulin (CaM)-activable activity and of affinity for CaM. It is also capable of antigenically cross-reacting with the *B.pertussis* AC.

A complex associating the active adenylate cyclase with the inactive, cross-reactive protein, is thus obtainable from *B.parapertussis* or variants expressing proteins with cross-reactivity.

The active and the inactive forms may thus be isolated by usual purification techniques.

Surprisingly, said adenylate cyclase preparations are obtainable from *B.parapertussis* while it was admitted that cross-immunity does not exist between *B.pertussis* and *B.parapertussis* infections.

This aspect of the invention is of great interest since *B.parapertussis* does not express, as it is well known, the Ptx, while said toxin is only expressed by *B.pertussis*.

Accordingly, the invention provides means for obtaining antigenic adenylate cyclase preparations devoid of the side-effects associated with Ptx, such as the risks of allergic encephalitis.

According to the method of the invention, antigenic AC preparations, free from Ptx, are obtainable from *B.parapertussis* (hemolytic) clones. Said clones are selected either in vitro or recovered from lung homogenates post challenge and are capable of inducing an acute edematous haemorragic alveolitis.

A specific hly$^+$ clone advantageously expressing high amounts of active AC was recovered from lungs and consists of 63-2S clone deposited under N•I-749 at the Collection Nationale de Culture de Microorganismes (CNCM), on Apr. 15, 1988.

The culture supernatants of 63-2S corresponding to standardized bacterial suspensions at $10^9$ CFU/ml have an AC enzymatic activity of about 20–25 units.

Hly$^{30}$ clones having a lower AC spontaneous expression can be injected by the intranasal route to mice, and reisolated from lungs, in order to increase the AC activity.

The derived clones maintaining hly$^+$, AC$^+$ phenotype expression enter into the scope of the invention. For example, 63-2TCS (trypto-casein-soy) has been obtained from 63-2S strain, growing on a non-specific medium with respect to Bordetellae with the same yield and maintaining hly$^+$, AC$^+$ expression.

A cross immunity between *B.pertussis* and *B.parapertussis* was evidenced by passive cross protection with anti-*B.pertussis* adenylate cyclase antibodies. The works carried out on adenylate cyclase preparations obtained according to the invention have shown that said molecules are protective antigens.

Accordingly said adenylate cyclase preparations are advantageously used according to the invention for making vaccine preparations, under the proviso that they do not give cross-reactions with the host adenylate cyclase. The adenylate cyclase preparations comprise both active and inactive proteins, or only one of said proteins.

Such vaccines, which are thus elaborated from adenylate cyclase preparations obtained from *B.parapertussis* are molecular vaccines and are capable of preventing Bordetella infections and toxic effects in human and animals. The usual doses and administration forms are advantageously used. The vaccines are preferably in the form of intranasal, oral or parenteral preparations.

In the vaccine compositions, the adenylate cyclase preparations may be associated with FHA in the same inoculum or not. FHA will then be administered at the same time as the adenylate cyclase preparation or at different times. FHA preparations are advantageously obtained using the method, for example, of Sato et al., in Infect. Immun., 1983, 41, 313–320 or Imaizumi et al., Journal of Microbiol. Methods, 2, 334–347 (1984).

The adenylate cyclase preparations may also be associated with purified AC preparations disclosed in said FR patent application 8615963 of Nov. 17, 1986, and optionally with FHA.

Advantageously, the vaccine compositions of the invention prevent the infection caused by Bordetella such as *B.pertussis, B.parapertussis, B.bronchiseptica* and *B.avium.*

According to another embodiment bacterial whole cell vaccines are elaborated from *B.parapertussis.* Such vaccines have a protective effect both against *B.parapertussis* and *B.pertussis.*

Other characteristics and advantages of the invention will be given in the following example, with reference to the figures.

The materials and methods used in the example are the followings:

a Bacterial strains and culture conditions

*B.pertussis* 18323 (ATCC 9797) and *B.parapertussis* (CIP63-2) were plated on Bordet Gengou agar medium supplemented with horse defibrinated blood (15% final) (BG), for selecting hemolytic (hly) or non hemolytic clones, which were subcultured in Stainer Scholte broth.

b Assays for AC and Ptx

Methods for detecting AC and Ptx, either from enzymatic or biological activities, or through Western blot analysis have been described by White A. A. et al., Methods Enzymol., 38C, 41–46, 1974, such as modified by Manoune et al., J. Biol. Chem., 252, 2039–2046, 1977.

c Infection of mice

Three weeks old, specified pathogen-free, Swiss OF1 female mice, weighing 16 g±1 were purchased from the ferme experimentale de Rennemoulin (Institut Pasteur, 78 Villepreux, France) and maintained by groups of 5 in cages topped with filter caps (Techniplast, UAR, France), on sterile litter, and fed with gamma-ray sterilized food (granules RO3, UAR, France) and autoclaved drinking water. The mice were infected at 4 weeks of age, after short ether anesthesia, by intranasal injection of standardized bacterial inocula (in a volume of 50 microlitres) from the *B.pertussis* strain Kendrick 18323 (type strain ATCC 9797), or the *B.parapertussis* CIP 63-2.

d Histopathology

Lungs from infected mice were collected at selected times fixed in 10% formaldehyde, embedded in paraffin, and serially sectioned before staining with hematoxilin and eosin or Giemsa, for light microscopy examination.

Results

KINETICS OF PULMONARY INFECTION WITH *B.PARAPERTUSSIS*

Two groups of mice were infected intranasally with inocula prepared from either an $hly^+$ clone selected on BG (63-2H) or said $hly^+$ clone, deposited under N• I 749 recovered from lung homogenates of mice at day 3 post challenge (63-2S).

The dose-effects of the intranasal infection are reported on FIG. 1, which gives, in function of days the variations of $log_{10}$ CFU/lungs (colony forming units) with 63-2H (curve • . . . •), and 63-2S (curve ▲_▲). The vertical bars are arithmetic means of 5 mice $^{\pm}$SEM.

As shown in FIG. 1, both inocula had similar virulence (in terms of bacterial growth/survival rate), whereas the clone 63-2S was significantly more pathogenic than the clone 63-2H. The intranasal injection of $10^3$ CFU corresponded to the LD50% in the case of 63-2S and only to the LD25% in the case of 63-2H.

HISTOPATHOLOGICAL FINDINGS

The lungs of mice dead at 24 h post challenge exhibited the typical AEHA observed with an $hly^+$ $AC^+$ clone derived from *B.pertussis* 18323, as reported by Brézin C. et al., in FEMS Microbiol. Lett. 42, 75–80, 1987.

AC ACTIVITIES

Dosages of AC in culture supernatants of 63-2S and 63-2H corresponding to standardized bacterial suspensions at $10^9$ CFU/ml, showed that AC enzymatic activities were of 20–25 units and 4–7 units respectively.

CROSS-IMMUNITY BETWEEN *B.PERTUSSIS* AND *B.PARAPERTUSSIS*

Immune response of *B.parapertussis* infected mice to AC:

Western blot analysis of urea extracts of *B.parapertussis* with specific polyclonal anti-AC antibodies was carried out.

The urea extracts were obtained as follows:

Bacterial pellets were homogenized in buffer A (Tris HCl 25 mM, $MgCl_2$ 6 mM, NP4O 0, 1%, pH8), (⅓; w/w) and the same amount of urea 8M in buffer A was added. The medium was stirred 40 min. at 30° C. A dialysis in buffer A was performed, followed by a centrifugation (5000g) 30 min. at 6° C. The supernatant is recovered and constitutes the urea extract.

The polyclonal anti-AC are obtained by immunizing animals with purified AC preparations obtained from *B.pertussis* and recovering the antibodies raised against the preparations from the immunserums.

Preferred AC preparations used for raising the antibodies consist in the purified AC preparations disclosed in FR patent application 86/15963 filed on Nov. 17, 1986, in the name of the applicant, relating to "Purified AC preparation, a method for obtaining the same and their biological applications".

Such preparations are characterized in that they possess a high degree of purity and are virtually totally devoid of contaminating bacterial substances, in particular pertussis toxins, lipopolysaccharide (or LPS) and filamentous hemagglutinin (or FHA). The AC is thus available in a homogeneous form, sedimenting with a S coefficient equal to 3.6 in a sucrose density gradient, which exists in two structurally related molecular forms of 45 and 43 kDa, respectively.

According to another aspect the preparations of AC are characterized in that they possess an activity which may attain and even exceed 1600 micromoles of cAMP min$^{-1}$. mg$^{-1}$.

Said purified AC preparations are obtainable by placing into contact with calmodulin a previously concentrated supernatant of bacterial cultures expressing adenylate cyclase or an extract of these bacteria.

The polyclonal antibodies are produced, for example, by immunizing animals such as the rabbit or the mouse by means of the AC preparations in question in which the AC is free or in the form of a complex with eucaryotic proteins, in particular with calmodulin, and by recovery of the antisera containing the antibodies and then of the antibodies themselves by standard methods.

The monoclonal antibodies are obtainable by fusion of a mouse myeloma with spleen lymphocytes derived from mice immunized with purified adenyl cyclase.

Monoclonal antibodies (8–25) are particularly used. They immunoprecipitate a triplet of 50,45 and 43 kDa as well as a protein of molecular weight higher than 100 kDa in crude extracts and preparations of the enzyme purified from bacterial cells.

PROTECTIVE EFFECTS OF ANTI-*B.PERTUSSIS* AC ANTIBODIES AGAINST THE RESPIRATORY LETHAL INFECTION OF THE MOUSE WITH *B.PARAPERTUSSIS* a) *B.parapertussis* inoculum was preincubated with polyclonal or monoclonal anti-*B.pertussis* AC antibodies. The results are given in table 1 below:

TABLE 1

| Antibodies | Normal serum | Polyclonal anti-AC | | | Monoclonal anti-AC | | |
|---|---|---|---|---|---|---|---|
| log$_{10}$ dilution | −1 | −1 | −2 | −3 | −1 | −2 | −3 |
| N° Survivors/ Total | 2/12 | 8/12 | 6/12 | 5/12 | 11/12 | 9/12 | 7/12 |

As shown in the table, said *B.parapertussis* inoculum incubated with polyclonal or monoclonal anti-*B.pertussis* AC antibodies inhibited the lethal challenge in a dose dependent fashion.

The cross-immunogenicity between *B.parapertussis* and *B.pertussis* was assessed by cross-vaccination experiments, as shown in table 2.

TABLE 2

CROSS-VACCINATION AGAINST *B. PERTUSSIS* OR *B. PARAPERTUSSIS*

| Immunogen[a] | BP AC$^+$ | | BP AC$^-$ | | BPP | | Controls | |
|---|---|---|---|---|---|---|---|---|
| Challenge[b] | BP AC$^+$ | BPP | BP AC$^+$ | BPP | BP AC$^+$ | BPP | BP AC$^+$ | BPP |
| Number survivors/ Total | 9/12 | 7/12 | 4/12 | 1/12 | 7/12 | 9/12 | 0/12 | 1/12 |

[a]Bacterial suspensions heated at 56° C. for 20 min.; two subcutaneous injections at 5 days interval of 1.2 × 10$^8$ *B. pertussis* AC$^+$ (BP AC$^+$), 2.5 × 10$^8$ *B. pertussis* AC$^-$ (BP AC$^-$) or 2.2 × 10$^9$ *B. parapertussis* 63-2S (BPP).
[b]Intranasal injection of 5 × 10$^7$ CFU (colony-forming units) of BP AC$^+$ or 8 × 10$^8$ CFU of BPP.

The hybridoma strain producing the monoclonal antibodies was deposited with the National Collection of Cultures of Microorganisms under the N• I-610 on the 9th of October 1986.

Figure 2:
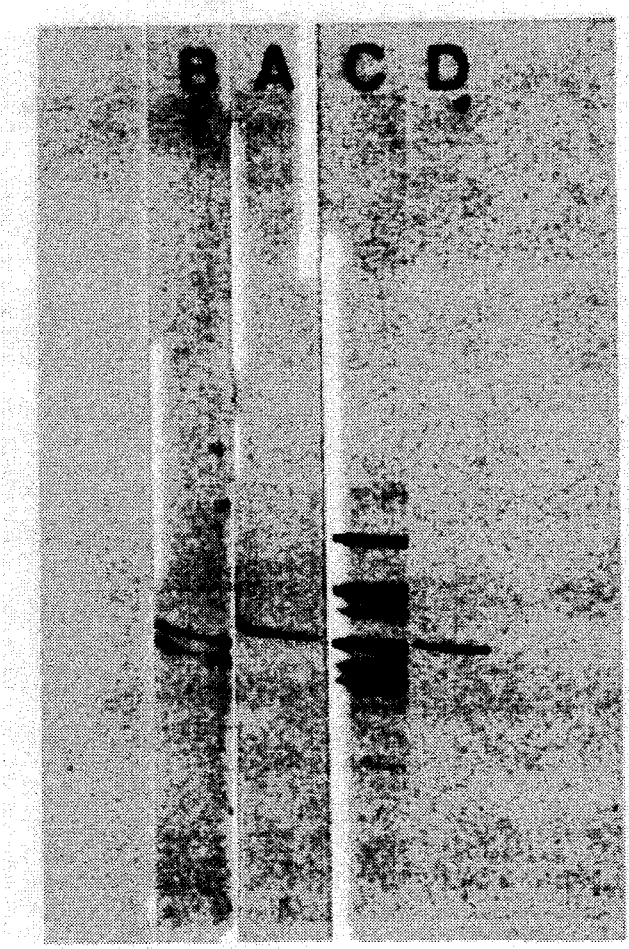
FIG. 2 represents immunoblots of AC-containing extracts from *B. parapertussis* and *B. pertussis* with polyclonal anti-*B. pertussis* AC antibodies.

The results are given on FIG. 2 wherein lanes 1 to 4 respectively correspond to:

1. *B.parapertussis* extracts, revealed with anti *B.pertussis* AC antibodies,
2. Purified *B.pertussis* AC revealed by serum from *B.parapertussis* infected mice,
3. *B.parapertussis* extract, revealed with serum from *B.parapertussis* infected mice,
4. *B.parapertussis* AC revealed in *B.parapertussis* extract with anti-*B pertussis* AC antibodies.

Said Western blot analysis revealed the presence of a Mr 43–45 kDa antigen which cross reacted with the *B.pertussis* AC (FIG. 2).

Moreover, comparative immunoblotting of the purified *B.pertussis* AC with serum from *B.parapertussis* convalescing mice, collected at day 27 post intranasal challenge (FIG. 1), revealed the presence of anti-*B.pertussis* AC antibodies.

We claim:

1. A method of obtaining an active and an inactive adenylate cyclase which are free from pertussis toxin and have specific reactivity with polyclonal or monoclonal antibodies to *Bordetella pertussis* adenylate cyclase, comprising culturing a hemolytic clone of *Bordetella parapertussis*, homogenizing the cultured *Bordetella parapertussis* to produce a homogenate and isolating active and inactive adenylate cyclase from the homogenate, wherein said inactive adenylate cyclase is devoid of calmodulin-activatable adenylate cyclase activity and of affinity for calmodulin.

2. The method of claim 1, wherein said active adenylate cyclase has a molecular weight of 43±4.3–45±4.5 kDa.

3. The method of claim 1, wherein said hemolytic clone of *Borderella parapertussis* induces an acute edematous hemorrhagic alveolitis, and is obtained (a) by in vitro cloning, or (b) from lung tissue of an animal following administration of said *Bordetella parapertussis* to said animal.

4. The method of claim 3, wherein said *Borderella parapertussis* is selected from the group consisting of clone 63-2S (CNCM No. I-749) and a clone derived therefrom, which is hemolytic and expresses adenylate cyclase.

5. The method of claim 4, wherein said *Borderella parapertussis* is clone 63-2S (CNCM No. I-749).

6. The method of claim 1, wherein the step of isolating the active and inactive adenylate cyclase from the culture comprises treating the homogenized *Borderella parapertussis* with urea.

7. A method of obtaining an inactive adenylate cyclase having a molecular weight 43±4.3–45±4.5 kDa which has specific reactivity with polyclonal or monoclonal antibodies of *Borderella parapertussis* adenylate cyclase and is devoid of calmodulin-activatable adenylate cyclase activity and of affinity for calmodulin, comprising culturing a hemolytic clone of *Borderella parapertussis*, homogenizing the cultured *Bordetella parapertussis*, separating active adenylate cyclase from inactive adenylate cyclase, and recovering inactive adenylate cyclase.

* * * * *

UNITED STATES PATENT AND TRADEMARK OFFICE
CERTIFICATE OF CORRECTION

PATENT NO. : 5,595,901
DATED : January 21, 1997
INVENTOR(S) : Rocancourt et al.

It is certified that error appears in the above-indentified patent and that said Letters Patent is hereby corrected as shown below:

In the Title

Delete the word "PROTECTIVE" from the title of the invention.

In the Abstract

Line 12, italicize the word "Bordetella".

In the Claims

Claim 3, line 2 (col. 6, line 59), delete "*Borderella*" and insert therefor --*Bordetella*--.

Claim 4, line 1 (col. 6, line 64), delete "*Borderella parap-*" and insert therefor --*Bordetella para---*; and line 2 (line 65), delete "*ertussis*" 1 and insert therefor --*pertussis*--.

Claim 5, line 1 (col. 7, line 1), delete "*Borderella parap-*" and insert therefor --*Bordetella para---*; and line 2 (line 2), delete "*ertussis*" and insert therefor --*pertussis*--.

Claim 6, line 3 (col. 7, line 5), delete "*Borderella*" and insert therefor --*Bordetella*--.

UNITED STATES PATENT AND TRADEMARK OFFICE
CERTIFICATE OF CORRECTION

PATENT NO. : 5,595,901  Page 2 of 2
DATED      : January 21, 1997
INVENTOR(S): Rocancourt, et al It is certified that error appears in the above-indentified patent and that said Letters Patent is hereby corrected as shown below:

Claim 7, line 4 (col. 7, line 10), delete "*Borderella*" and insert therefor --*Bordetella*--; and line 7 (col. 8, line 3), delete "*Borderella*" and insert therefor --*Bordetella*--.

Signed and Sealed this

Nineteenth Day of August, 1997

Attest:

BRUCE LEHMAN

*Attesting Officer*  *Commissioner of Patents and Trademarks*